US012114970B2

(12) United States Patent
Bersch et al.

(10) Patent No.: US 12,114,970 B2
(45) Date of Patent: *Oct. 15, 2024

(54) METHOD AND APPARATUS FOR SIMULATING, MEASURING AND RECORDING A SUBJECT'S ABILITY TO PERFORM A VARYING RANGE OF BARRIER REACHES

(71) Applicant: PROGRESSIVEHEALTH COMPANIES, LLC, Houston, TX (US)

(72) Inventors: Keith Bersch, Evansville, IN (US); Patrick Staples, Peachtree City, GA (US); Ricky Lockard, Newburgh, IN (US); Donald Osgood, Evansville, IN (US); Phillip Chumbley, Aurora, IL (US)

(73) Assignee: ProgressiveHealthCompanies, LLC, Houston, TX (US)

( * ) Notice: Subject to any disclaimer, the term of this patent is extended or adjusted under 35 U.S.C. 154(b) by 403 days.

This patent is subject to a terminal disclaimer.

(21) Appl. No.: 17/683,003

(22) Filed: Feb. 28, 2022

(65) Prior Publication Data

US 2022/0378327 A1    Dec. 1, 2022

Related U.S. Application Data

(63) Continuation-in-part of application No. 15/424,869, filed on Feb. 5, 2017, now Pat. No. 11,262,175.

(51) Int. Cl.
*A61B 5/11*    (2006.01)
*A61B 5/00*    (2006.01)

(52) U.S. Cl.
CPC .......... *A61B 5/1114* (2013.01); *A61B 5/1116* (2013.01); *A61B 5/1121* (2013.01); *A61B 5/1126* (2013.01); *A61B 5/45* (2013.01)

(58) Field of Classification Search
CPC ........ A61B 5/1114; A61B 5/45; A61B 5/1126
See application file for complete search history.

(56) References Cited

U.S. PATENT DOCUMENTS

| 4,858,126 A | 8/1989 | Croce, Jr. |
| 5,562,104 A | 10/1996 | Hochberg et al. |

(Continued)

FOREIGN PATENT DOCUMENTS

| CN | 203663325 | 6/2014 |
| CN | 203861230 | 10/2014 |

(Continued)

*Primary Examiner* — Natalie Huls
*Assistant Examiner* — Nyla Gavia
(74) *Attorney, Agent, or Firm* — Martin IP Law Group; C. Richard Martin

(57) ABSTRACT

A method and apparatus for simulating, measuring and recording a subject's ability to perform a varying range of barrier reaches is provided. The apparatus includes a variable barrier reach instrument for simulating an actual barrier that the subject may lean against in performing a work task The variable barrier reach instrument may include a physical barrier having a substantially horizontal upper surface at a height above a base point. A sensing and recording device may be positioned proximate to the variable barrier reach instrument for sensing and recording a plurality of barrier reach data points as the subject bends forward against the physical barrier. A computer and an associated software program are also provided into which the recorded data points are entered. An algorithm may be contained within the software program that generates an interpolated arc reflecting the subject's reach at the physical barrier height from the recorded data points. Storage means associated with the computer are further provided for storing the interpolated arc and recorded data points.

20 Claims, 20 Drawing Sheets

(56) References Cited

U.S. PATENT DOCUMENTS

| | | | |
|---|---|---|---|
| 5,830,160 A * | 11/1998 | Reinkensmeyer | A61B 5/224 |
| | | | 600/595 |
| 6,227,047 B1 | 5/2001 | Livingston | |
| 6,599,045 B1 | 7/2003 | Kolb | |
| 8,348,811 B2 | 1/2013 | Kamins | |
| 8,915,868 B1 * | 12/2014 | Anderson | A61B 5/4561 |
| | | | 33/511 |
| 9,269,151 B2 | 2/2016 | Zahand | |
| 9,295,422 B2 * | 3/2016 | Tai | A63B 21/0442 |
| 2006/0028457 A1 | 2/2006 | Burns | |
| 2008/0133297 A1 | 6/2008 | Schmotzer | |
| 2010/0179453 A1 | 7/2010 | Schweighofer et al. | |
| 2010/0190617 A1 | 7/2010 | Gautier | |
| 2013/0324857 A1 | 12/2013 | Kurillo et al. | |
| 2015/0293525 A1 | 10/2015 | Yamamoto et al. | |
| 2016/0070958 A1 | 3/2016 | Whelan et al. | |
| 2016/0081594 A1 | 3/2016 | Gaddipati et al. | |
| 2018/0221712 A1 | 8/2018 | Bersch et al. | |

FOREIGN PATENT DOCUMENTS

| | | | | |
|---|---|---|---|---|
| GB | 2330912 A * | 5/1999 | | A61B 5/103 |
| JP | 10105536 A * | 4/1998 | | |
| JP | 25467996 | 4/1998 | | |
| JP | 2005066233 | 8/2003 | | |
| JP | 4407208 | 2/2010 | | |
| KR | 20130038684 | 4/2013 | | |
| KR | 101276734 | 6/2013 | | |
| WO | 1997038845 | 10/1997 | | |
| WO | 2012108422 | 8/2012 | | |

\* cited by examiner

METHOD AND APPARATUS FOR SIMULATING, MEASURING AND RECORDING A SUBJECT'S ABILITY TO PERFORM A VARYING RANGE OF BARRIER REACHES

BACKGROUND OF THE INVENTION

Field of the Invention

The present invention relates to devices and processes for sampling, testing and measuring the range of motion and reach range of a test subject. More specifically, the present invention relates to a method and apparatus for sampling, testing and measuring a subject's ability to perform barrier-impeded reaches at varying barrier heights.

Description of the Problem

In the manufacturing industry, and more particularly in the automobile assembly industry, assembly line workers are required to perform a variety of reach tasks as part of their duties in assembling a vehicle. Those duties include reaching inside the engine compartment to install various components, reaching into the interior of the vehicle to install various interior components such as the dash assembly. Many of these tasks have a common feature that a creates barrier in the form of a part of the car, for example the fender where a worker is reaching into the engine compartment from the side of a vehicle, limits the worker's reach.

Some workers, based on their size, reach and/or range of motion are more adept at performing certain reach tasks that occur in the assembly process. Accordingly, there is a need for a method and apparatus that accurately and systematically measures the reach of assembly line workers at a variety of barrier heights to optimize the process of assigning tasks to assembly line workers.

SUMMARY OF THE INVENTION

It is therefore an objective of the present invention to provide a system and apparatus for systematically measuring the reach of a subject such as an assembly line worker given a variety of barrier heights.

It is also an objective of the invention to provide a systematic method for gathering and recording the barrier reach performance results of a subject, such as an assembly line worker, so that he/she may be assigned to assembly tasks that best suit his/her reaching abilities. Further, the invention will allow for the collection of barrier reach data such that manufacturers can design/redesign tasks so that those tasks are better matched to their employee/candidate population.

The present invention meets these objectives by providing an apparatus for simulating, measuring and recording a subject's ability to perform a varying range of barrier reaches. The apparatus includes a variable barrier reach instrument for simulating an actual barrier that the subject may lean against in performing a work task. The variable barrier reach instrument may include a physical barrier having a substantially horizontal upper surface at a height above a base point. A sensing and recording device is positioned proximate to the variable barrier reach instrument for sensing and recording a plurality of barrier reach data points as the subject bends forward against the physical barrier. A computer and an associated software program into which the recorded data points are entered, and an algorithm contained within the software program that generates an interpolated arc reflecting said subject's reach at the physical barrier height from the recorded data points are provided, as is storage means associated with the computer for storing the interpolated arc and recorded data points.

According to one aspect of the invention, the height of the barrier is adjustable, and may include a plurality of pre-set variable heights. The barrier may preferably include seven pre-set variable heights ranging in 6-inch increments from 24 inches to 60 inches.

According to another aspect of the invention, a drive mechanism is attached to the physical barrier for moving the physical barrier vertically relative to the base point. A pair of vertical posts, spaced a distance apart may be provided, with the physical barrier positioned between the vertical posts. A pair of gear boxes associated with the pair of vertical posts may be provided. The gear boxes are affixed to the physical barrier and configured for vertical translational movement relative to the vertical posts. A motor may be attached to one of the gear boxes for imparting motion to the pair of gearboxes and the physical barrier relative to the vertical posts.

According to a further aspect of the invention, the sensing and recording device comprises a bar for grasping by the subject, and one or more encoders attached to the bar for sensing and recording linear and angular displacement of the bar. A cable may be provided having a first end attached to the bar and a second end attached to one of the one or more encoders. The one or more encoders may include a linear encoder attached to a second end of the cable and configured to sense and record an amount of cable that is withdrawn from the linear encoder at various times, and a rotary encoder slidably engaging the cable along a length thereof and configured to sense and record the angular displacement of the bar and cable at various times.

In yet another aspect of the invention, the plurality of data points include at least a start point (Max Y) where the subject is positioned with its feet at the base point and its hands grasping the bar extended overhead as high as possible, an end point (Min Y) where the subject is positioned bent forward against the physical barrier at the lowest point in the vertical (y) axis above the base point, a furthest horizontal point (Max X) at a point on the arc in the horizontal (x) axis farthest from the base point, a first point that is midway between the start point and the furthest horizontal point, and a second point that is midway between the end point and the furthest horizontal point.

According to yet another aspect of the invention, there is provided a method for simulating, measuring and recording a subject's ability to perform a varying range of barrier reaches. The method includes the steps of: (1) positioning the subject at a variable barrier reach instrument for simulating an actual barrier that the subject may lean against in performing a work task, the variable barrier reach instrument having a physical barrier having a substantially horizontal upper surface at a height above a base point; (2) having the subject grasp a bar that is operatively connected to a sensing and recording device positioned proximate to the physical barrier; (3) having the subject raise the bar overhead such that the sensing and recording device is operatively engaged; (4) having the subject bend forward, while continuing to grasp the bar with outstretched arms, extending the bar in an arc until the subject has reached a lowest point nearest to the base point; (5) using the sensing and recording device to sense and record in a software program associated with a computer a plurality of data points along an arc that is generated as the subject bends forward; (6) applying an algorithm contained in the software program to said recorded data points to generate an interpolated arc reflecting the subject's reach at the physical barrier height from the recorded data points, and (7) storing the interpolated arc and recorded data points in storage means associated with the computer.

According to a further aspect of the invention, the method may include the further step of adjusting the height of the barrier and repeating steps (1)-(6) at the adjusted barrier height. Steps (1)-(6) may be repeated sequentially for seven pre-set variable heights ranging in 6-inch increments from 24 inches to 60 inches. The step of positioning a subject at a barrier includes having the subject come into contact with said barrier.

A further aspect of the present invention involves the step of adjusting the height of the physical barrier by actuating a drive mechanism attached to the physical barrier to move the physical barrier vertically relative to the base point.

The step of identifying and recording the plurality of data points may comprise the steps of: identifying and recording a start point (Max Y) on the sensing and recording device where the subject is positioned with its feet at the base point and its hands grasping the bar extended overhead as high as possible; identifying and recording an end point (Min Y) on the sensing and recording device where an arc sensed and recorded on the two-dimensional grid as the subject bends forward against the physical barrier comes to an end at the lowest point in the vertical (y) axis above the base point; identifying and recording a furthest horizontal point (Max X) at a point on the arc in the horizontal (x) axis farthest from the base point; identifying and recording a first point that is midway between the start point and the furthest horizontal point; and identifying and recording a second point that is midway between the end point and the furthest horizontal point.

The step of using said sensing and recording device to sense and record may comprise using one or more encoders attached to the bar for sensing and recording linear and angular displacement of the bar. The step of using one or more encoders may further comprise using a linear encoder attached to the bar by a cable to sense and record an amount of cable that is withdrawn from the linear encoder at various times; and using a rotary encoder slidably engaging the cable along a length thereof to sense and record the angular displacement of the bar and cable at various times.

These and other objectives, features, and advantages of the present invention will become apparent from a review of the following drawings and detailed description of the preferred embodiments of the invention.

BRIEF DESCRIPTION OF THE DRAWINGS

The present invention can best be understood in connection with the accompanying drawings. It is noted that the invention is not limited to the precise embodiments shown in the drawings, in which.

DETAILED DESCRIPTION OF THE INVENTION

Figure 1:
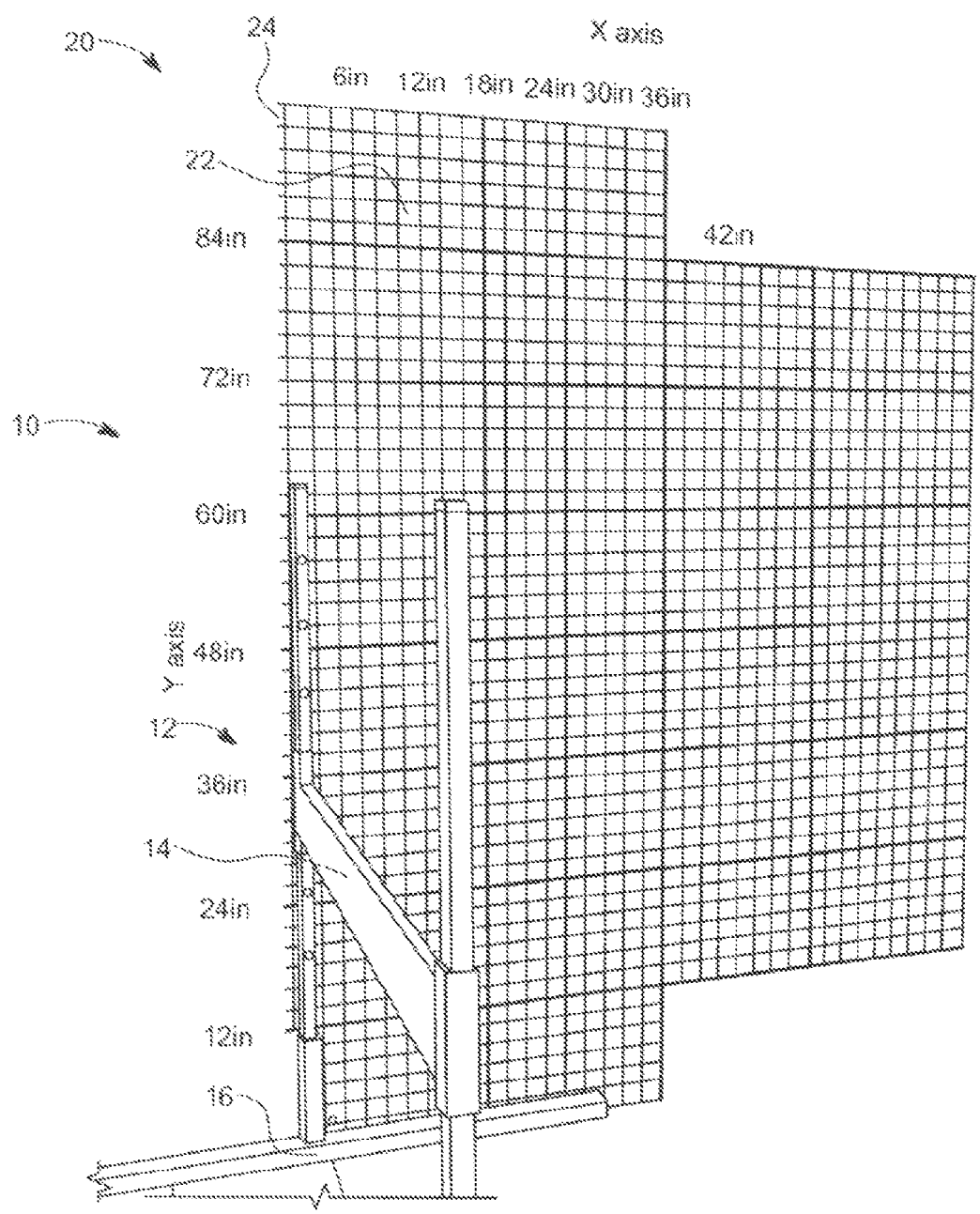
FIG. 1 is a side elevation view of an apparatus for measuring an individual's ability to perform a varying range of barrier reaches according to one presently preferred embodiment of the invention.

For purposes of promoting and understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

As best shown in FIG. 1-FIG. 3C, one presently preferred embodiment of the invention comprises an apparatus 10 for measuring a subject's S ability to perform a varying range of barrier reaches. The apparatus 10 includes a variable barrier reach instrument 12 having a substantially horizontal barrier 14 at a height (h) above a base point 16 (0,0). The variable barrier reach instrument 12 is used to simulate a barrier that the person or subject S would be leaning against.

Figure 5:
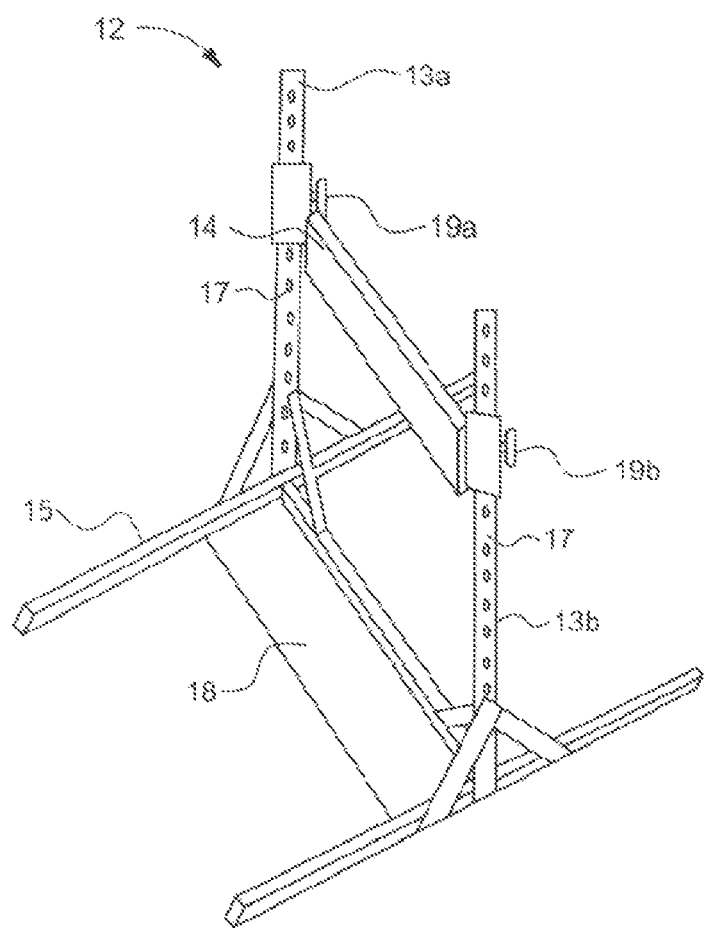
FIG. 5 is a perspective view of the adjustable-height barrier shown in FIG. 1.

As best shown in FIG. 5, the barrier reach instrument 12 includes a pair of vertical frame posts 13a, 13b supported by a base 15. The vertical posts 13a, 13b include a plurality of openings 17 therein for receiving removable securing pins 19 which are used to adjust the height of the barrier 14 so that different measurements can be obtained. According to a presently preferred embodiment of the invention, the barrier 14 moves vertically along a two frame posts 13a, 13b, and locks into place with spring loaded pins 19a, 19b.

While various heights and dimensions are anticipated, the variable barrier reach instrument 12 according to a presently preferred embodiment has a 4'×4'4" base 15 with two 62.5" vertical posts 13a, 13b, a 4'×12" non-slip foot plate 18, and a 4'×6" horizontal barrier 14. The barrier 14 can be set at various points starting at 18" to 60". Preferably, each vertical post 13a, 13b includes seven (7) pre-set openings for height adjustment ranging in 6-inch increments from 24 inches high to 60 inches high. The base 15 and vertical posts 13a, 13b may be constructed of any suitable material, including 2"×2"×⅛" square steel tubing. The barrier 14 may be of any dimension, and is preferably approximately 6 inches wide with a slight curvature.

Figure 3A:
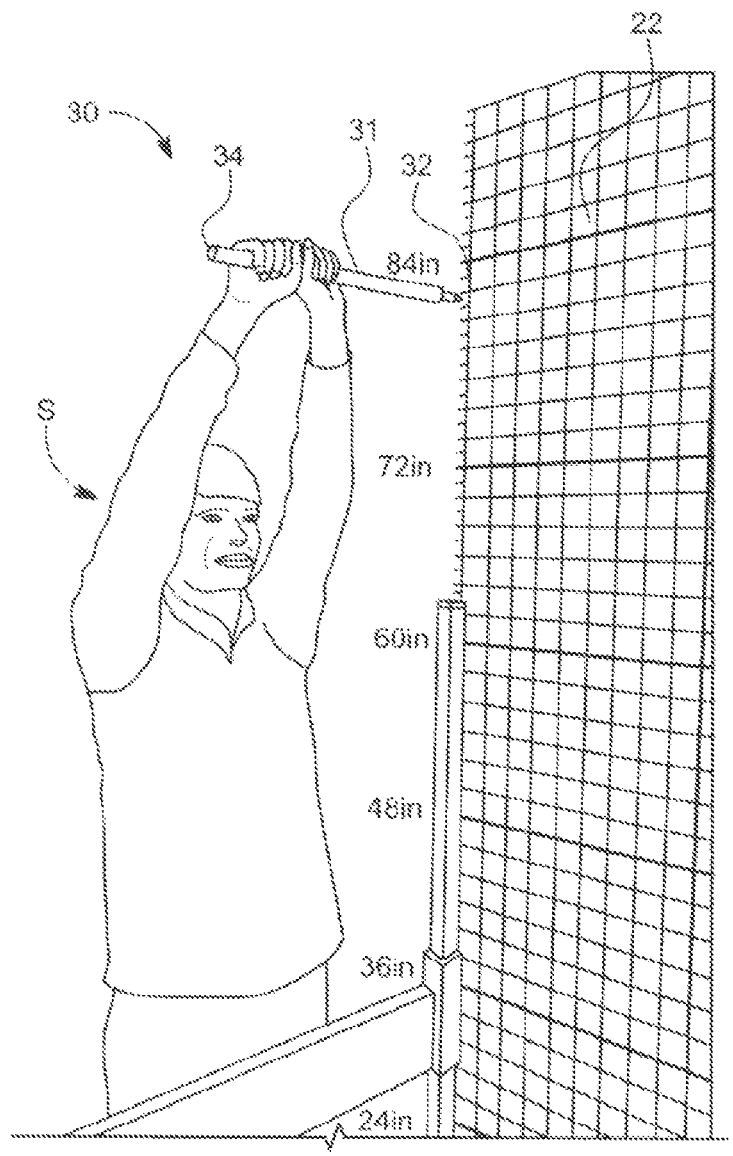
FIG. 3A is a side elevation view of a subject in the start position (Max Y) for performing the method for measuring an individual's ability to perform a varying range of barrier reaches according to a presently preferred embodiment of the invention.

During functional testing, the subject S steps onto the foot plate 18 and while maintaining contact with the barrier 14, grasps a rod 31 and raises the rod 31 overhead as high as possible (see FIG. 3A). While, maintaining contact with the barrier 14, the candidate then reaches as far forward and downward as possible, creating an arc A of motion (see FIG. 3B and FIG. 3C). It is important for accuracy purposes that the dowel rod 31 remains horizontal and perpendicular to the grid 22 through the entire process.

Figure 2:
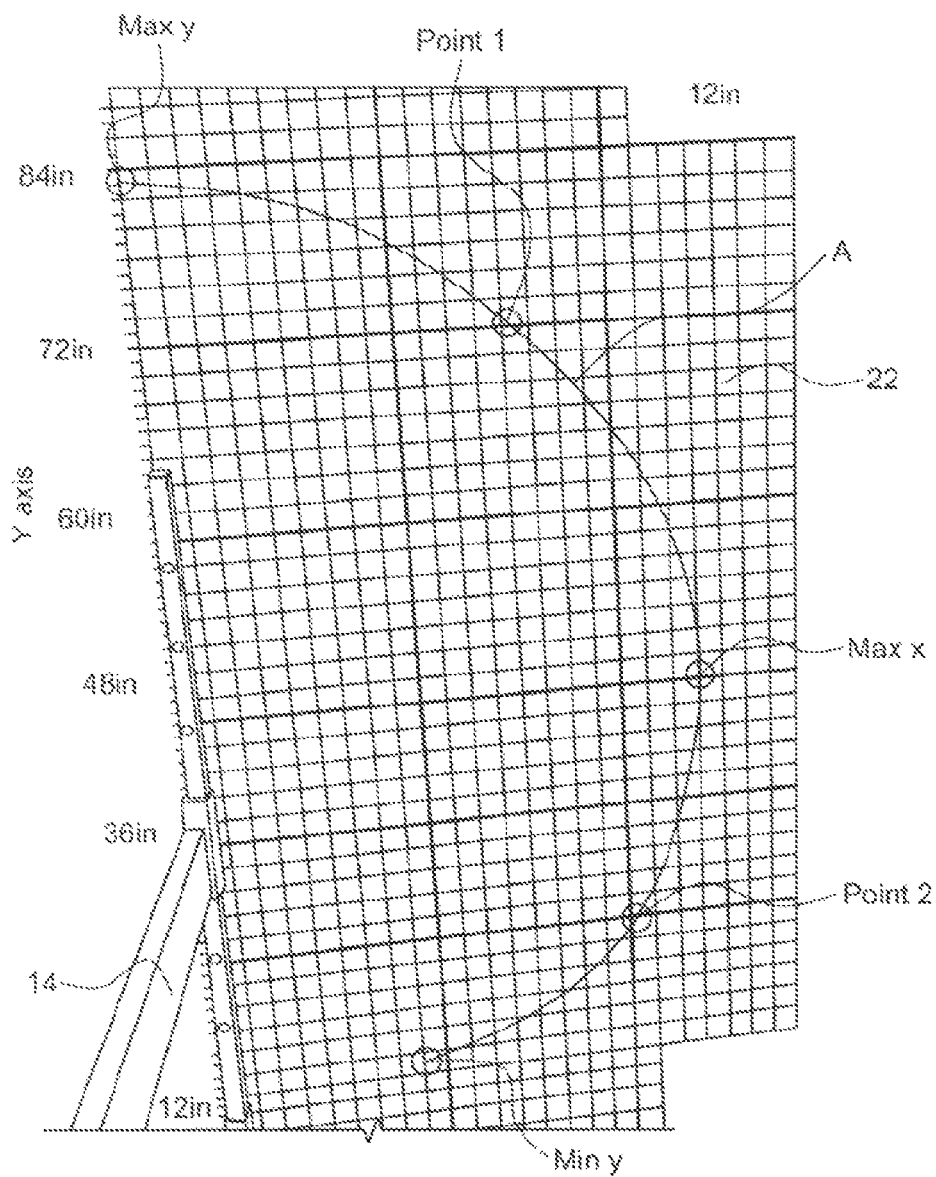
FIG. 2 is a side view in elevation of a portion of the apparatus shown in FIG. 1 with an example arc drawn on the sensing and recording device of the invention.

As most clearly shown in FIG. 2, the start point (Max Y) on the two-dimensional grid 22 is the point where the subject S is positioned with its feet at the base point 16 and its hands grasping a marking device 30 extended overhead as high as possible (see FIG. 3A). End point (Min Y) is the point on the two-dimensional grid 22 where an arc A is sensed and recorded on the two-dimensional grid 22 as the subject S bends forward against the barrier 14 and comes to an end at the lowest point in the vertical (y) axis above the base point 16 (see FIG. 3C). The furthest horizontal point (Max X) is at a point on the arc A in the horizontal (x) axis furthest from the base point 16. The first point (Point 1) is the point that is midway between the start point (Max Y) and the furthest horizontal point (Max X). Lastly, the second point (Point 2) is a point that is midway between the end point (Min Y) and the furthest horizontal point (Max X).

A method for measuring a subject's ability to perform a varying range of barrier reaches is also provided according to the invention. As shown in FIG. 3A, the subject S is positioned at the barrier 14. The subject S is instructed to stand as far forward on the foot plate 18 of the variable barrier reach instrument 12 as possible, coming into contact with the barrier 14. The subject S grasps the marking device 30 which has a first end 32 that engages the sensing and recording device 20. The subject S raises the marking device 30 overhead as high as possible, without over-extending the shoulders or elbows, such that the first end 32 engages a surface 24 of the sensing and recording device 20, which is positioned adjacent to the barrier 14.

Figure 3B:
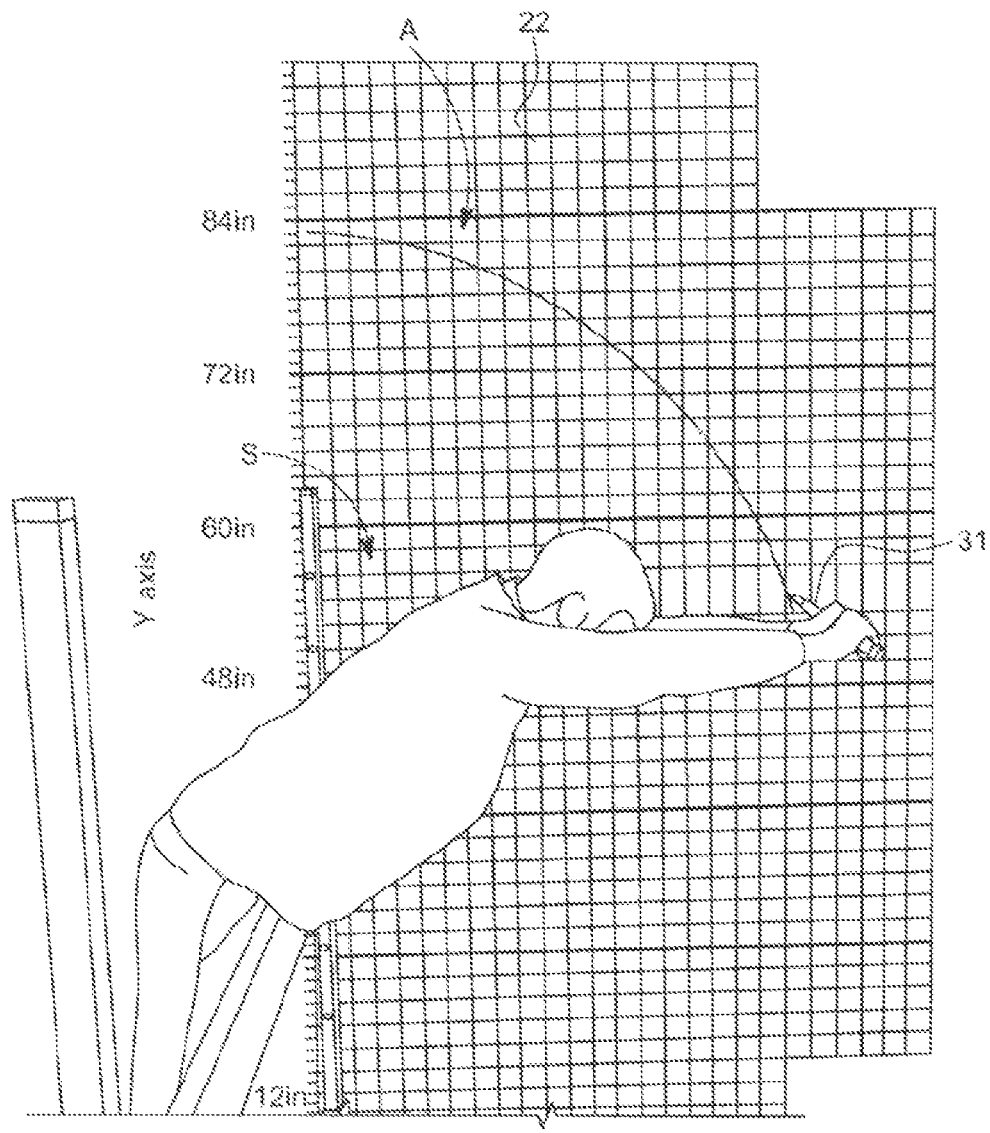
FIG. 3B is a side elevation view of a subject in an intermediate position for performing the method for measuring an individual's ability to perform a varying range of barrier reaches according to a presently preferred embodiment of the invention.
Figure 3C:
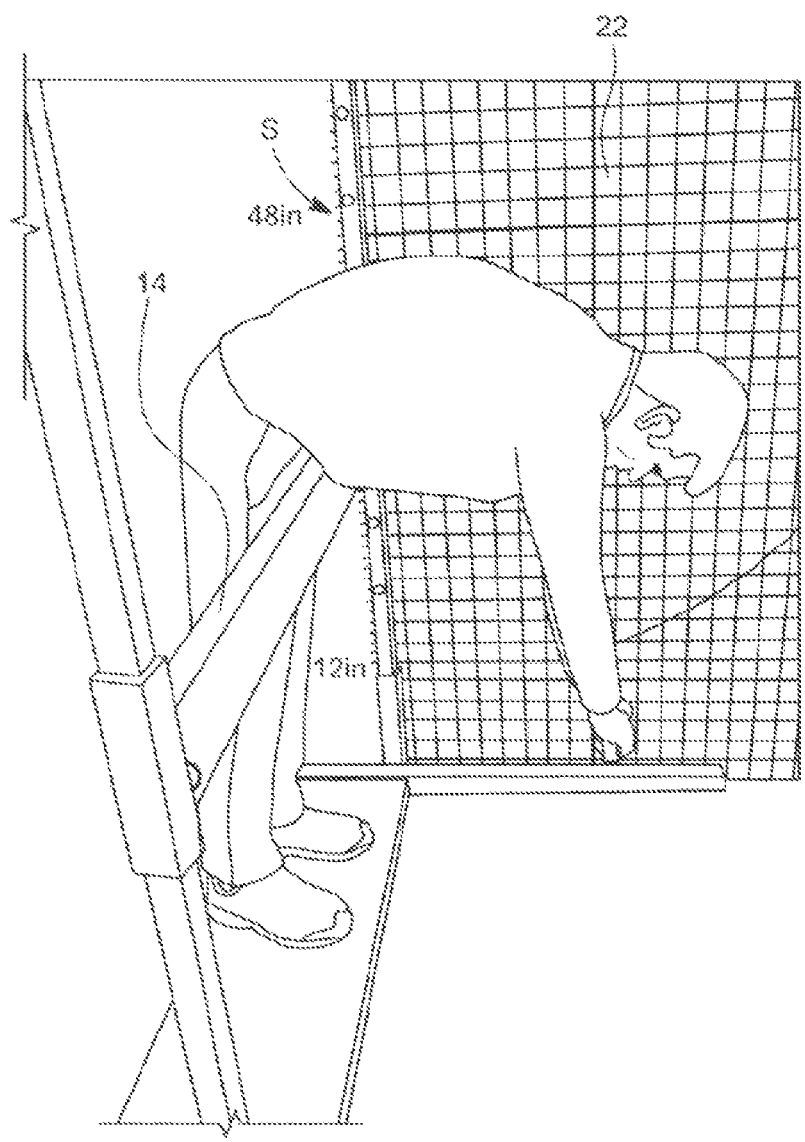
FIG. 3C is a side elevation view of a subject in the end position (Min Y) for performing the method for measuring an individual's ability to perform a varying range of barrier reaches according to a presently preferred embodiment of the invention.
Figure 4A:
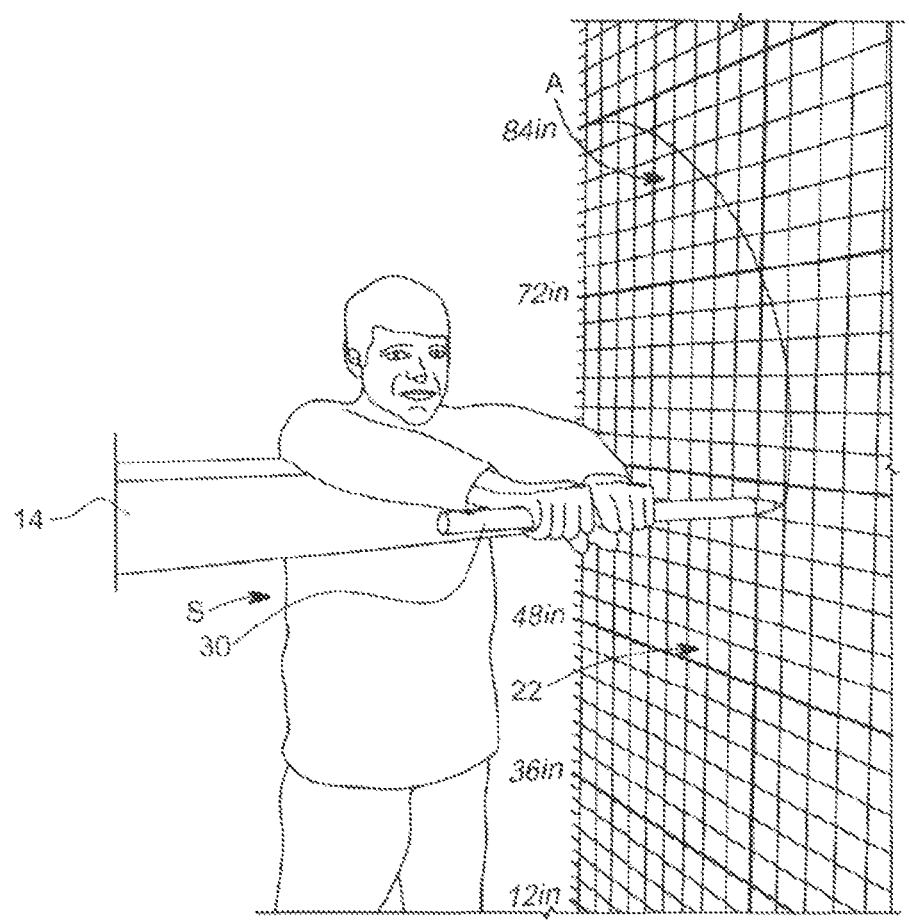
FIG. 4A is a side elevation view of a subject performing the method for measuring an individual's ability to perform a varying range of barrier reaches with the barrier in the maximum height position such that the end point (Min Y) corresponds with the furthest horizontal point (Max X), according to a presently preferred embodiment of the invention.
Figure 4B:
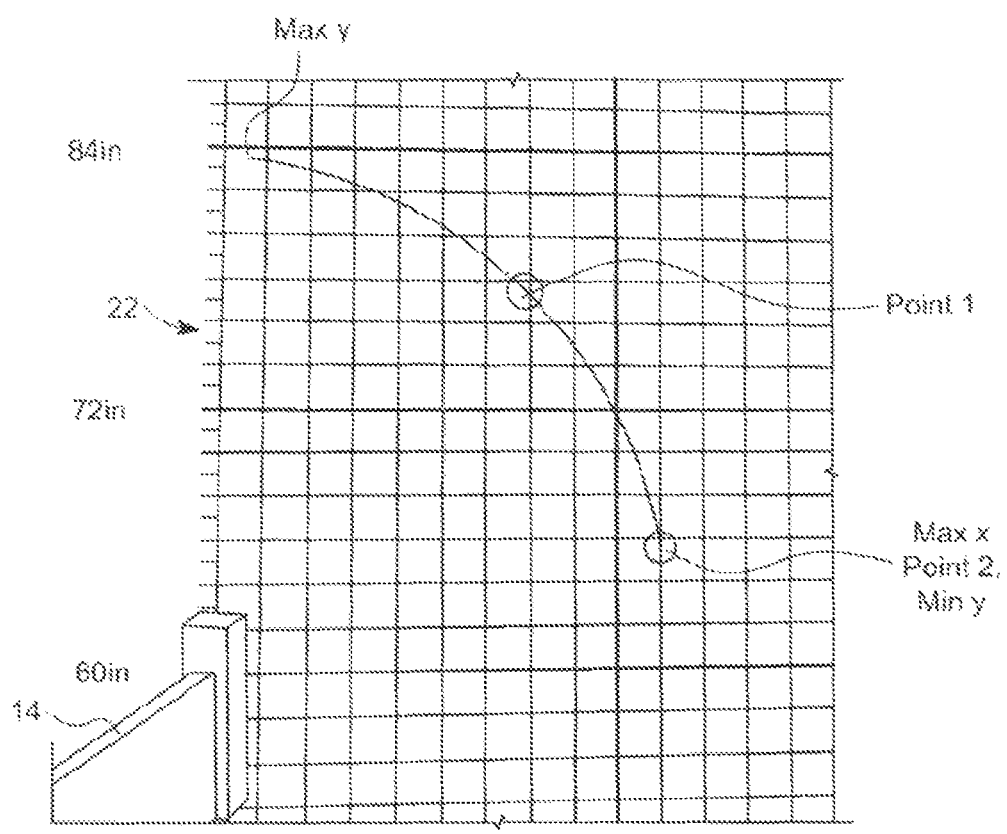
FIG. 4B is a side view in elevation of a portion of the apparatus shown in FIG. 4A with an example arc drawn on the sensing and recording device of the invention performed by the subject in FIG. 4A.

Next, as shown in FIG. 3B, the subject S bends forward, while maintaining contact between the first end 32 of the marking device 30 and the surface 24 of the sensing and recording device 20 thereby drawing an arc A within the grid 22 on the surface 24 of the sensing and recording device 20. The subject S continues to bend forward, reaching as far forward and downward as possible until the subject reaches the maximum point of extension, Min Y, as shown in FIG. 3C. Balance should be maintained throughout the entire arc, and the subject's heels should remain in contact with the foot plate 18. The subject S then returns to an upright position. The resulting arc A includes a plurality of data points, Max Y, Point 1, Max X, Point 2 and Min Y, which are identified, as discussed herein, and recorded. The recorded data points are then converted into an interpolated arc A' reflecting the subject's reach at a measured barrier height.

The method further includes the step of adjusting the height of the barrier and repeating the steps enumerated above for the new barrier height. This may be done at multiple barrier heights to obtain data for a subject S at several different barrier heights. According to one preferred embodiment of the method of the present invention, the process is repeated at seven pre-set variable heights ranging in 6-inch increments from 24 inches to 60 inches. Heights above and below that range are also anticipated depending on the specific needs of the test and the height of the subject.

Figure 6:
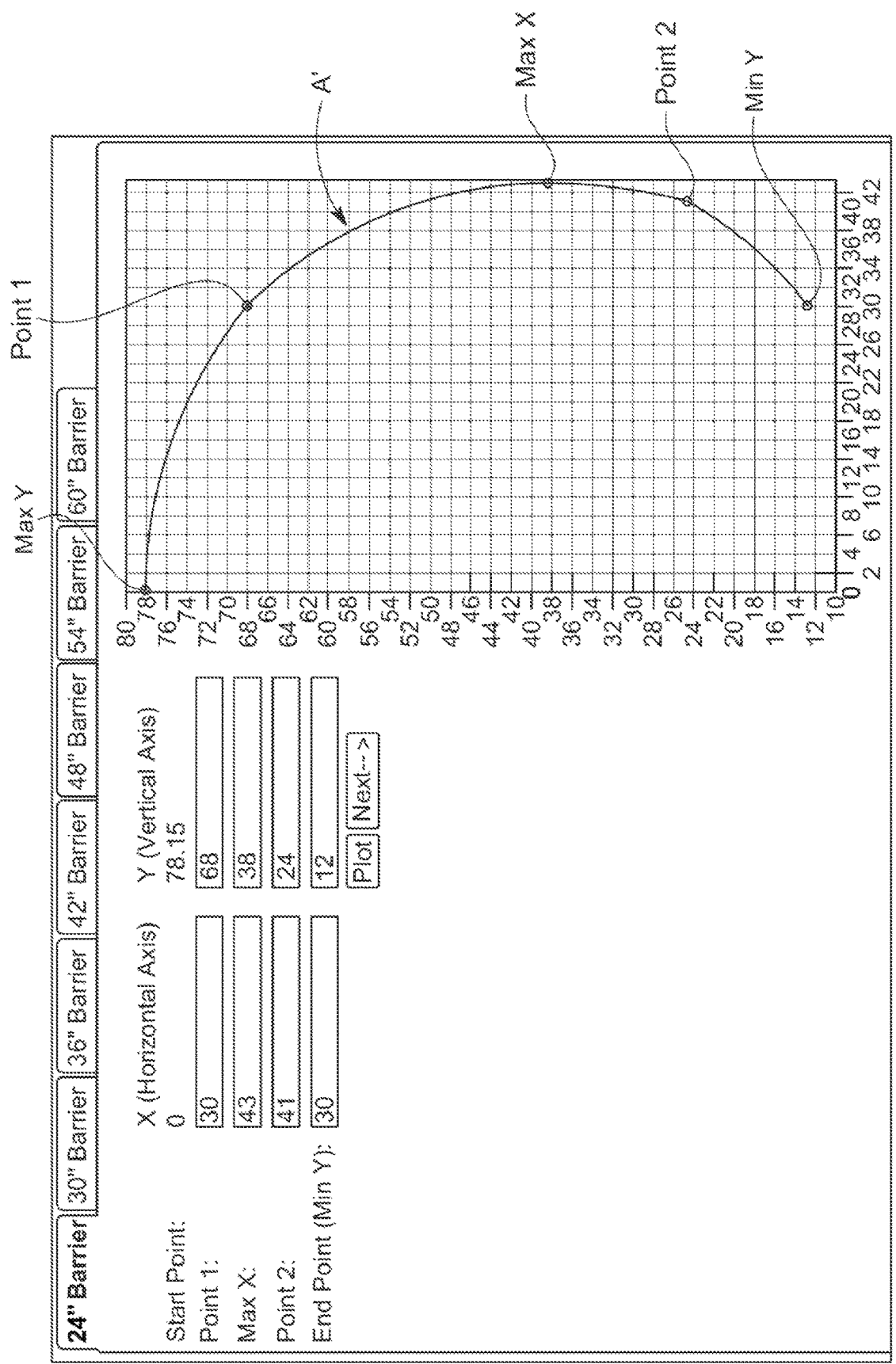
FIG. 6 is a diagram showing the step of identifying and recording data points according to a preferred embodiment of the invention.

The data points Max Y, Point 1, Max X, Point 2 and Min Y for each barrier height are recorded, for example, as shown in FIG. 6, in a computer software program. The five (5)—Max Y, Point 1, Max X, Point 2 and Min Y—x, y coordinates for each of the 7 barrier heights measured, ranging from 24"-60" are recorded. Each point is preferably entered as a whole number (rounding down). The user then selects 'Plot' in the software program to visually verify the generated arc A' vs. the candidate's actual drawn arc A. If the generated arc A' is >1.5 inch variance, the operator should verify the recorded points Max Y, Point 1, Max X, Point 2, Min Y again. The data is then entered for each of the next succeeding barrier heights and verified. Once all of the data points for all of the barrier heights are entered, the operator clicks "Save" to save the data.

As shown in FIG. 5A and FIG. 5B, at higher barrier heights, a subject S may not be able to draw arc beyond Point 1. In this situation, the same coordinates apply to and are entered for Max X, Point 2 and End Point. If a subject S cannot draw an arc A at all, the Start Point Max Y is entered for all subsequent data points.

Processing means for converting the data points into an interpolated arc reflecting said subject's reach at a barrier height are also provided. The processing means generally consist of a computer processor (CPU) running a software program containing applicants' proprietary algorithms for interpolating the arc.

When using the system shown in FIG. 1-FIG. 4B, the five points (Max Y, Point 1, Max X, Point 2, Min Y) are measured and recorded for each desired barrier height. Then, from these five points, the processing means of the system will extrapolate (per the proprietary algorithm) the entire curve (all data points) for all measured barrier heights.

If reach is to be assessed for a barrier height that is between two measured barrier heights (27" for example)—a new reach curve associated with the barrier height between the two nearest measured barrier heights (24" and 30" in the example) is derived by linear interpolation with the proportional distance among the respective x and y coordinates of the new curve and the respective points (all points, not just five points) on the curves from the measured barrier heights equaling the proportional distance of the barrier height to be assessed relative to the heights of the nearest above and below barrier heights.

Figure 7:
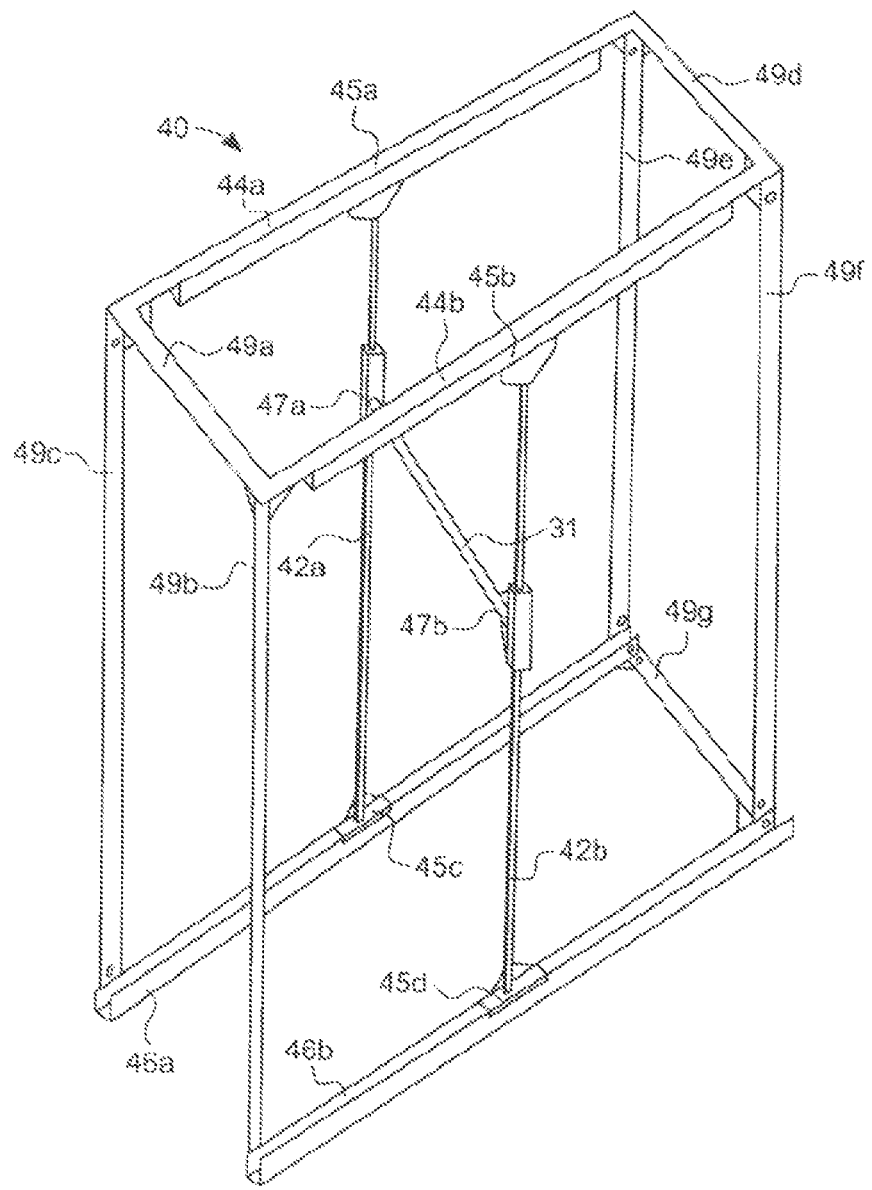
FIG. 7 is a perspective view of a reach rack frame that can be used in conjunction with the apparatus shown in FIG. 1.
Figure 8A:
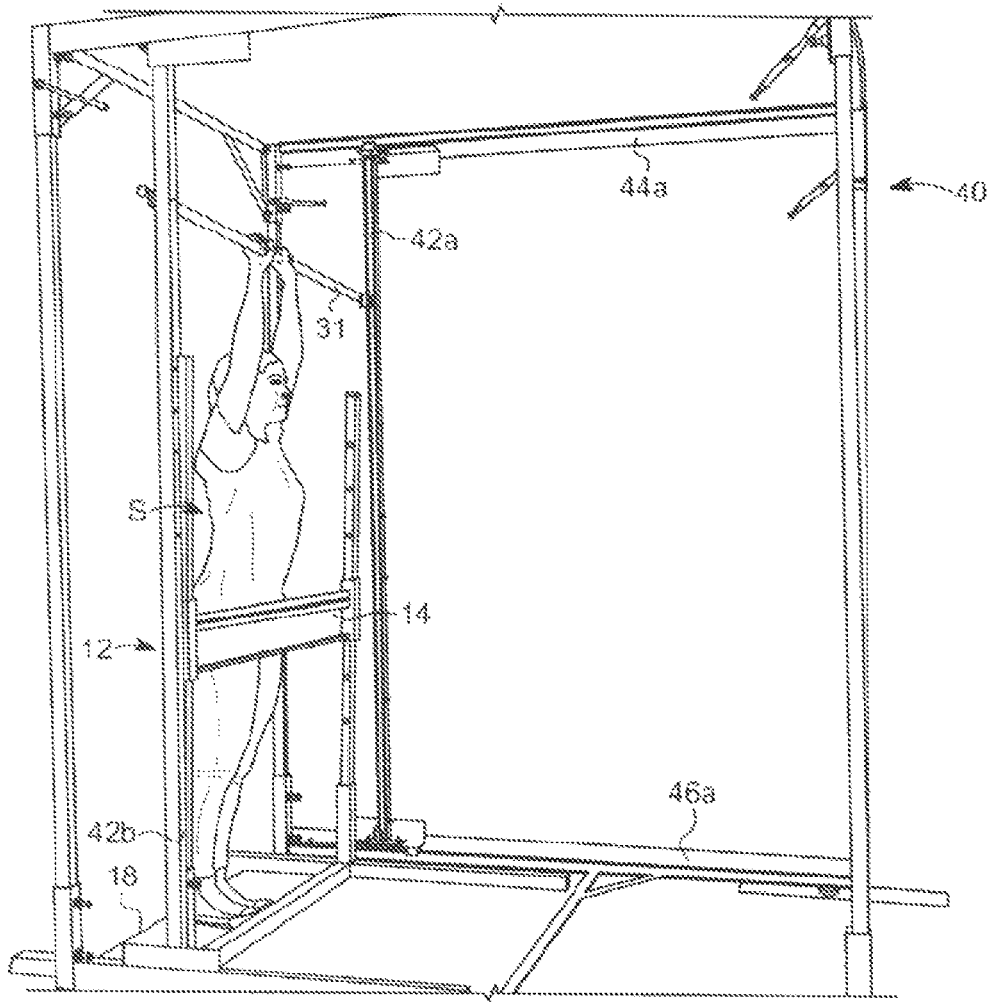
FIG. 8A is a side elevation view of a subject in the start position (Max Y) for performing the method for measuring an individual's ability to perform a varying range of barrier reaches incorporating the reach rack shown in FIG. 7.
Figure 8B:
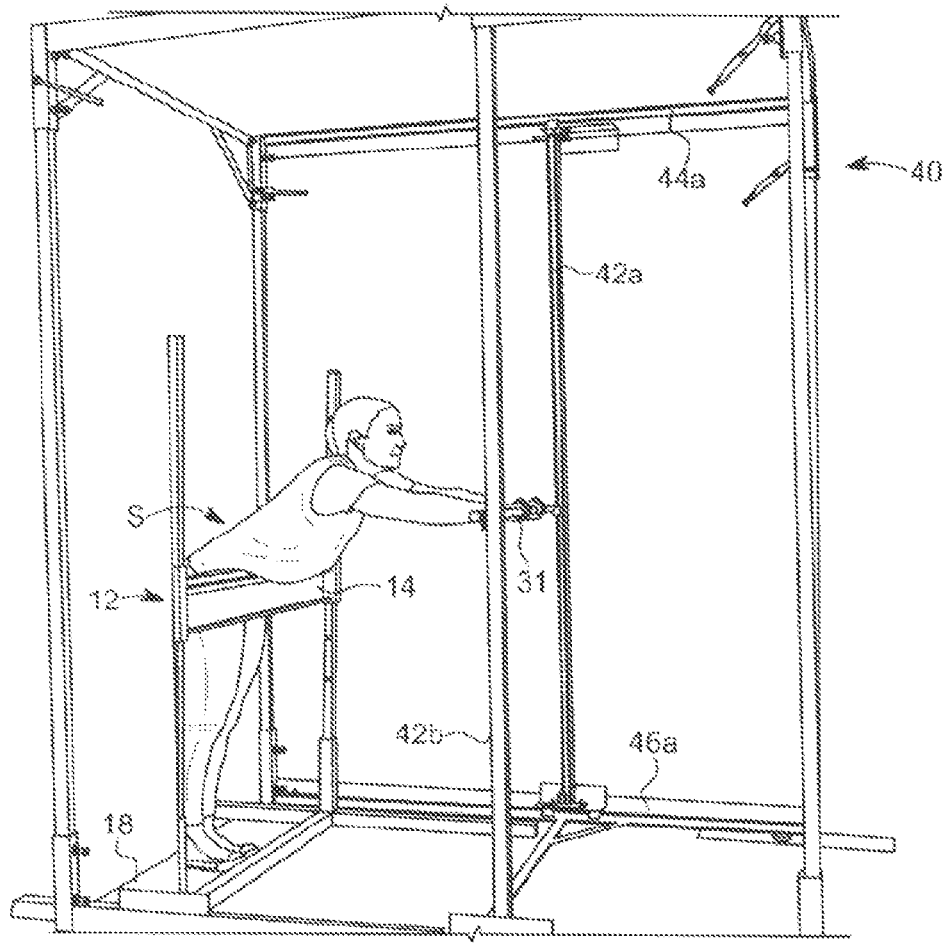
FIG. 8B is a side elevation view of a subject in an intermediate position for performing the method for measuring an individual's ability to perform a varying range of barrier reaches incorporating the reach rack shown in FIG. 7.

A further embodiment of the invention wherein the marking 30 device is contained within a variable barrier reach frame 40 that controls the movement of the marking device 30 relative to the sensing and recording device 20 is shown in FIG. 7-FIG. 8B.

The variable barrier reach frame 40 includes a first substantially vertical support rod 42a attached to the first end 32 of the marking device 30 and a second substantially vertical support rod 42b slideably attached to the second end 34 for controlling the movement of the marking device 30 in the vertical (y) axis relative to the base point 16. The reach rack frame 40 further includes an upper substantially horizontal pair of slide channels 44a, 44b which slideably engage upper ends of said first and second substantially vertical support rods 42a, 42b, and a lower substantially horizontal pair of slide channels 46a, 46b which slideably engage lower ends of said first and second substantially vertical support rods 42a, 42b for controlling the movement of the marking device 30 in the horizontal (x) axis relative to the base point 16.

The Variable Barrier Reach Frame 40 is intended to provide stability for full range of max reach and capture x,y coordinates while using the reach instrument. The Variable Barrier Reach Frame 40 may be of any suitable dimension, but for the average subject has a 4'10"×6'×9' frame with approximately 6' of linear rails along the top 44a, 44b and bottom 46a, 46b of each side. The linear rails 44a, 44b, 46a, 46b may be formed of any suitable material, but preferably are formed of 3"×3"×3"×⅛" C-shaped steel channel. The linear rails 44a, 44b, 46a, 46b are connected with vertical shafts 42a, 42b and a horizontal bar 31 allowing for simultaneous horizontal and vertical movement. Single bearing linear slides 45a, 45b, 45c, 45d are attached to the ends of the vertical shafts 42a, 42b and are slideably received in the grooves of linear rails 44a, 44b, 46a, 46b, respectively. The bar 31 may include a pair of pillow blocks 47a, 47b at the ends thereof for slideably engaging the round vertical shafts 42a, 42b.

Sensors capture x,y coordinates along horizontal and vertical rulers attached to the frame 40. The sensors may be affixed to the variable barrier reach frame 40 or they may be located near the frame and sense and measure movement of the bar 31. Alternatively, the variable barrier reach frame can be incorporated into the system of the primary embodiment such that the sensing and recording device 20 is positioned adjacent to the barrier reach instrument 12 and the variable barrier reach frame 40 for sensing and recording a plurality of data points (Max Y, Point 1, Max X, Point 2, Min Y). Additional bracing supports 49a, 49b, 49c, 49d, 49e, 49f, 49g, which are preferably formed from 3"×3"×⅛" angle steel, may be provided at the ends of the linear rails 42a, 42b, 44a, 44b to provide additional support to the variable barrier reach frame 40.

As shown in FIG. 8A, during functional testing, the subject S steps onto the foot plate 18 on Variable Barrier Reach Instrument 12, grasps the bar 31 and raises the bar 31 overhead as high as possible. While, maintaining contact with the barrier 14, the subject S then reaches as far forward and downward as possible (FIG. 8B), creating an arc of motion, as has been generally described herein.

The sensor(s) associated with the barrier reach frame 40 sense and record the entire reach curve, i.e. ALL data points of the curves associated with each measured barrier height, is automatically recorded in the system—not just the "five points." As above, if reach is to be assessed for a barrier height that is between two measured barrier heights (27" for example)—a new reach curve associated with the barrier height between the two nearest measured barrier heights (24" and 30" in the example) is derived by linear interpolation with the proportional distance among the respective x and y coordinates of the new curve and the respective points (all points, not just five points) on the curves from the measured barrier heights equaling the proportional distance of the barrier height to be assessed relative to the heights of the nearest above and below barrier heights.

As best shown in FIG. 9-FIG. 13, an alternative embodiment of the invention is provided that comprises an apparatus 110 for measuring a subject's S ability to perform a varying range of barrier reaches. The apparatus 110 includes a variable barrier reach instrument 112 having a substantially horizontal barrier 114 at a height (h) above a base point (0,0). The variable barrier reach instrument 112 is used to simulate a barrier that the person or subject S would be leaning against.

Figure 9:
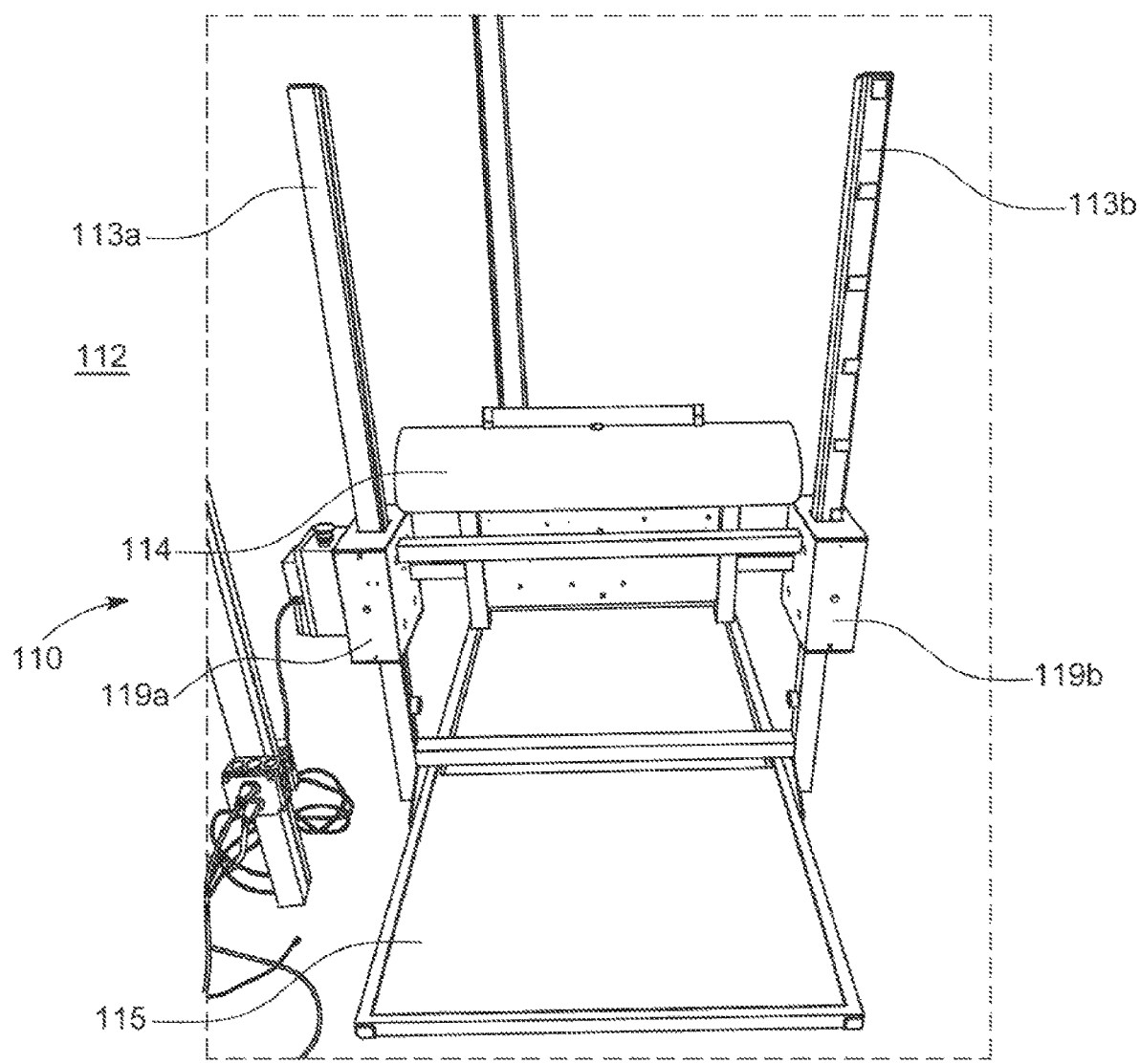
FIG. 9 is a front elevation view of an apparatus for simulating, measuring and recording a subject's ability to perform a varying range of barrier reaches according to an alternative embodiment of the invention.
Figure 10:
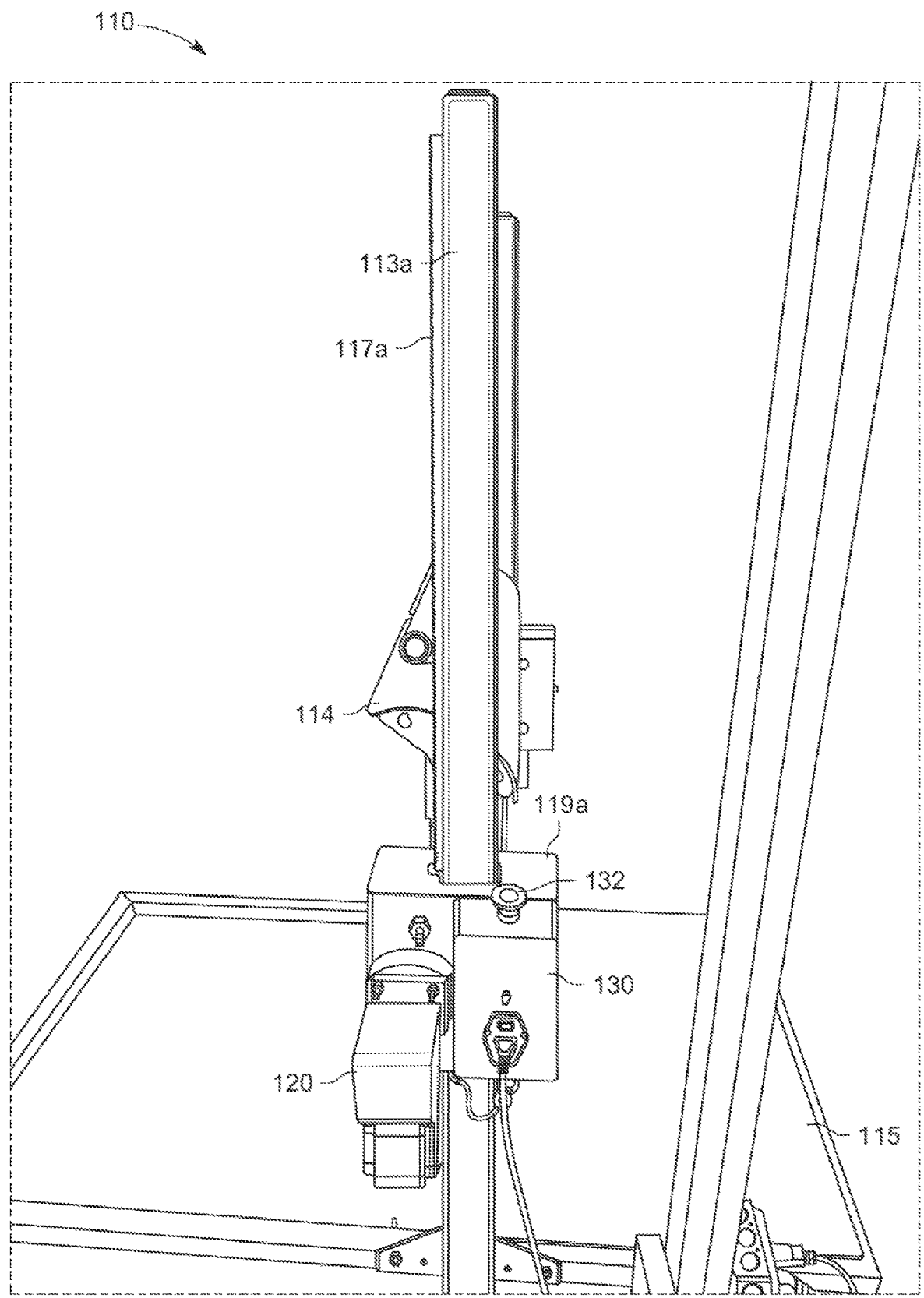
FIG. 10 is a side elevation view of the apparatus shown in FIG. 9.

As best shown in FIG. 9 and FIG. 10, a barrier reach instrument 112 includes a pair of vertical frame posts 113a, 113b supported by a base 115. Each vertical post 113a, 113b include a track 117a, 117b that extends substantially the entire length of the corresponding post. The teeth on the outer face of each track 117a, 117b engage one or more gears (not shown) located inside gearboxes 119a, 119b which surround the respective posts 113a, 113b and are affixed to the horizontal barrier 114. A stepper motor 120 is attached to one of the gearboxes 119a for driving the gearboxes 119a, 119b carrying the horizontal barrier 114 along the tracks 117a, 117b to raise or lower the horizontal barrier 114 to a desired height. An emergency stop mechanism 130, including an emergency stop button 132, is also provided and is configured to stop movement of the gearboxes 119a, 119b along the tracks 117a, 117b upon actuation.

Figure 11:
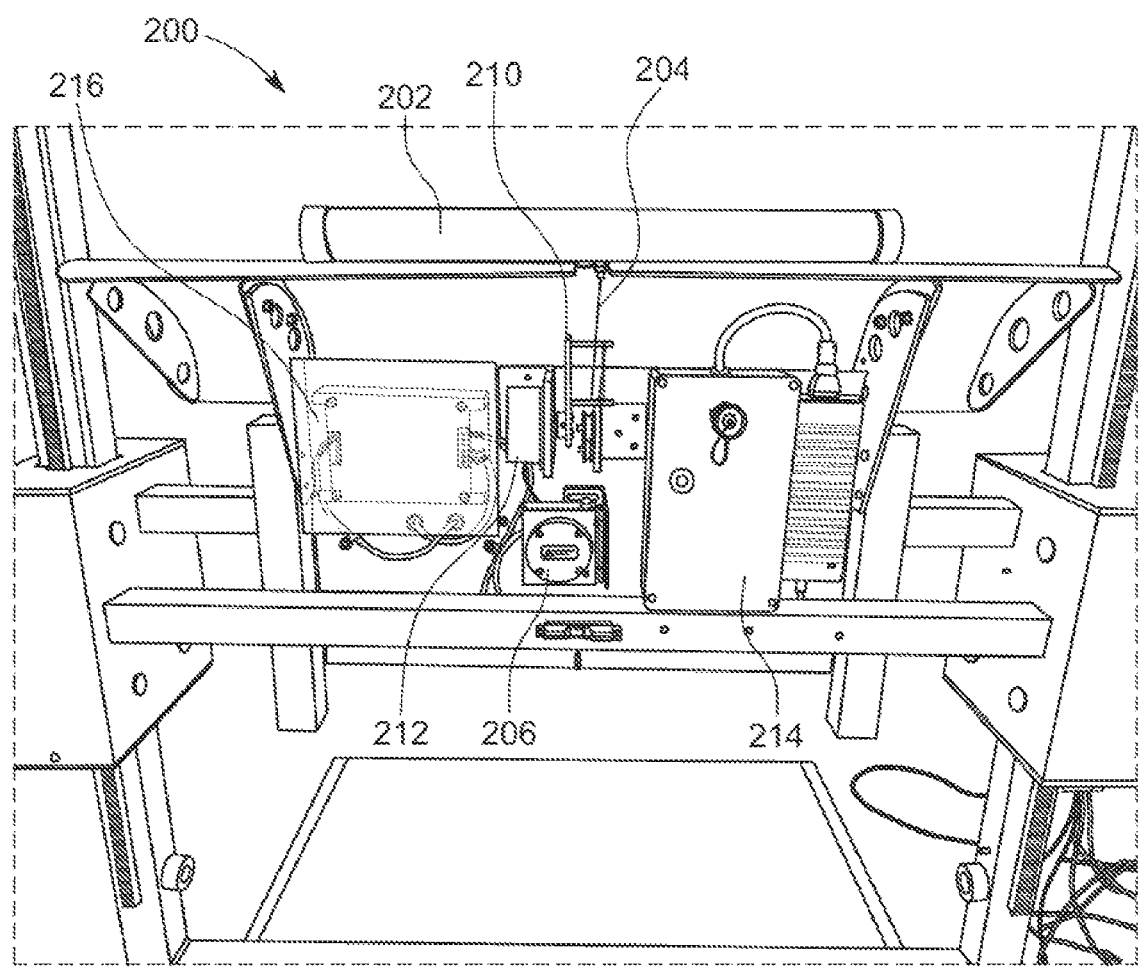
FIG. 11 is rear elevation view of the sensing and recording device portion of the apparatus shown in FIGS. 9 & 10.
Figure 12:
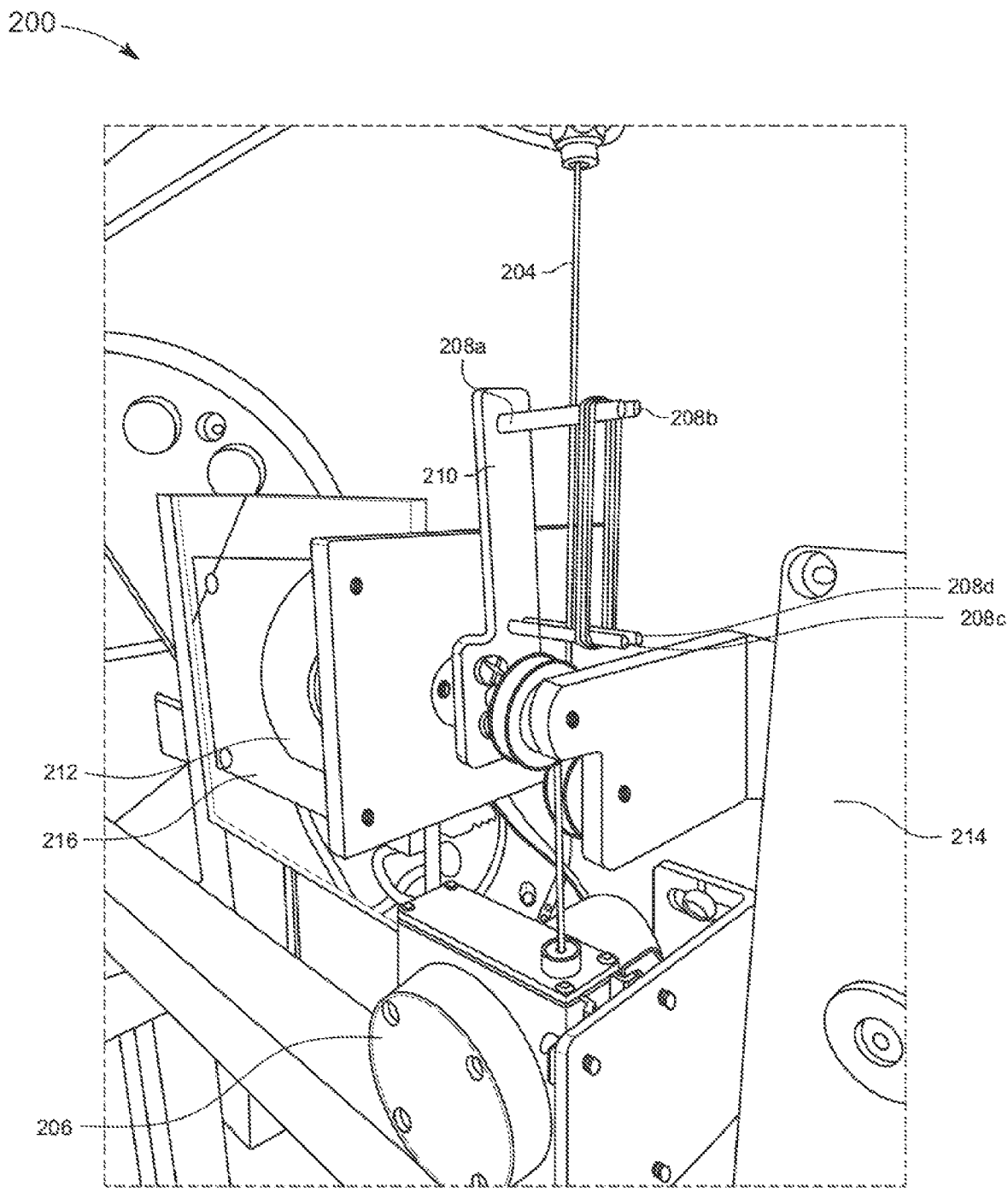
FIG. 12 is a perspective view of the sensing and recording device portion shown in FIG. 11.

As shown in FIG. 11 and FIG. 12, a sensing and recording device 200 is positioned proximate to the horizontal barrier 114 and includes a bar 202 for grasping by the subject S. The first end of a cable 204 is attached to the bar 202 at or near the center thereof. A second end of the cable 204 is attached to a linear encoder 206. A portion of the length of cable 204 is wrapped around a spool in the linear encoder 206, and as the bar 202 is raised, the cable 204 is unwound from the spool and the linear encoder 206 measures the length of the cable 204 as it is unwound from the spool. Between the linear encoder 206 and bar 202, the length of cable 204 passes through pins 208a, 208b, and pins 208c, 208d of pivot arm 210 of a rotary encoder 212. As the bar 202 moves forward or back, the cable 204 engages one or the other of pins 208a, 208b and 208c, 208d causing the arm 210 to rotate relative to the rotary encoder 212, which measures the degree of rotation.

The linear encoder 206 and rotary encoder 212 measure and collect data during use of the device. That data is electronically transferred to a processor 214, such as an Arduino, having hardware and software for receiving the inputs from the linear encoder 206 and rotary encoder 212 and processing that data into useable information. A power source 216 is also provided to power the components of the sensing and recording device 200.

Figure 13:
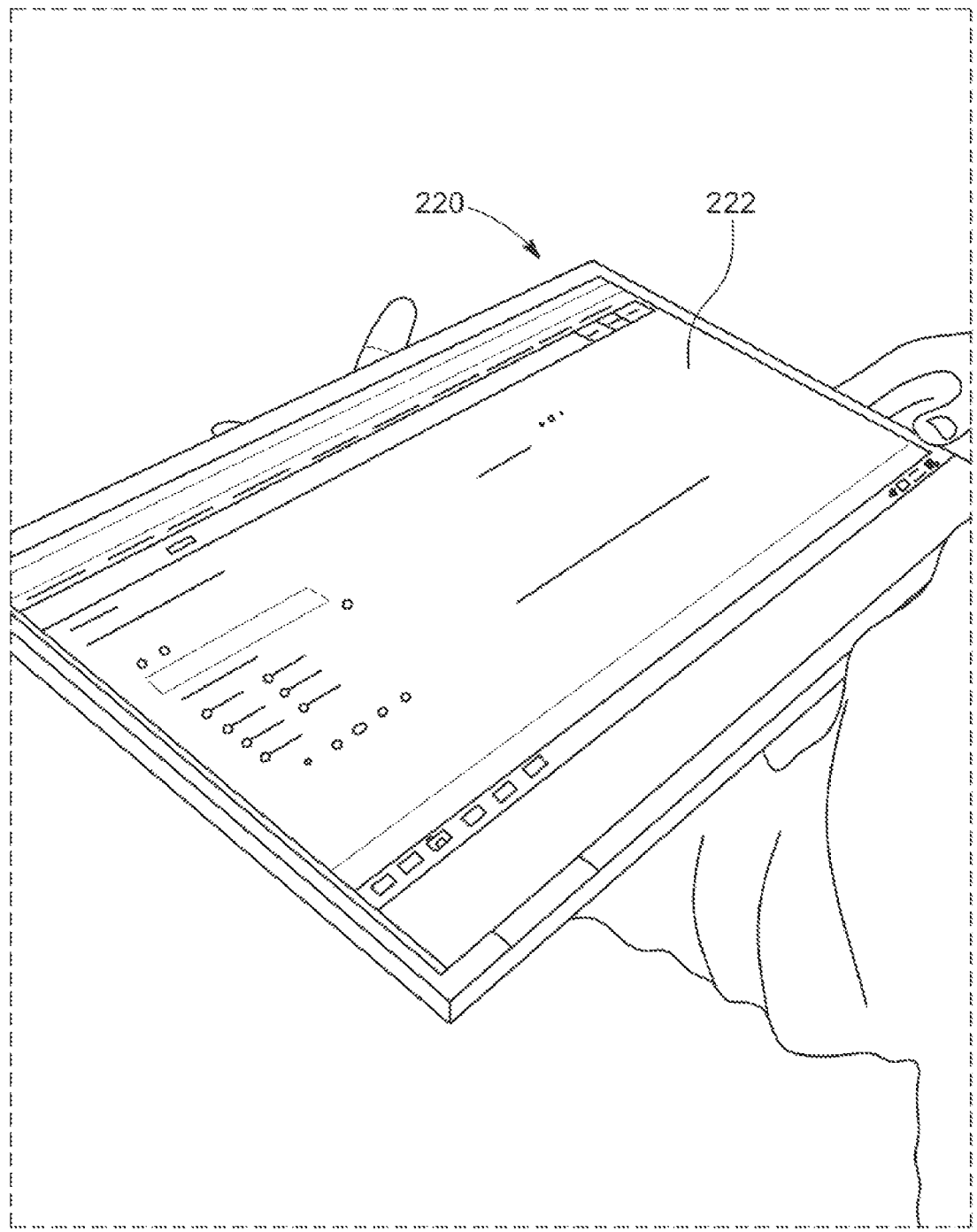
FIG. 13 is a perspective view of a user interface module for use in connection with the apparatus shown in FIGS. 9-12.

A user interface module, such as a tablet computer 220 as shown in FIG. 13 is in communication with the processor 214. The user interface module can be in wireless communication with the processor 214 by known wireless communication platforms such as WiFi and/or Bluetooth. Alternatively, the user interface module 220 can be hard-wired to the processor 214 via cabling (non shown) connected to standard USB or other ports on the processor and user interface module 220. The user interface module 220 may include a display screen 222, which may be a touch-screen display. The display screen can be used to display prompts for user input and to display data in graphic format from the linear encoder 206 and rotary encoder 212.

To initiate the method for measuring a subject's ability to perform a varying range of barrier reaches, a user U first selects a subject and enters pertinent information for that subject in the user interface module 220. The user U would next select the specific barrier height to be used for that measurement (i.e. 24"). That information is relayed to the processor 214, and, if the barrier is not already at the desired height, the stepper motor 120 is engaged to turn the gears in the gearboxes 119a, 119b to raise or lower the barrier 114 to the desired height.

Figure 14A:
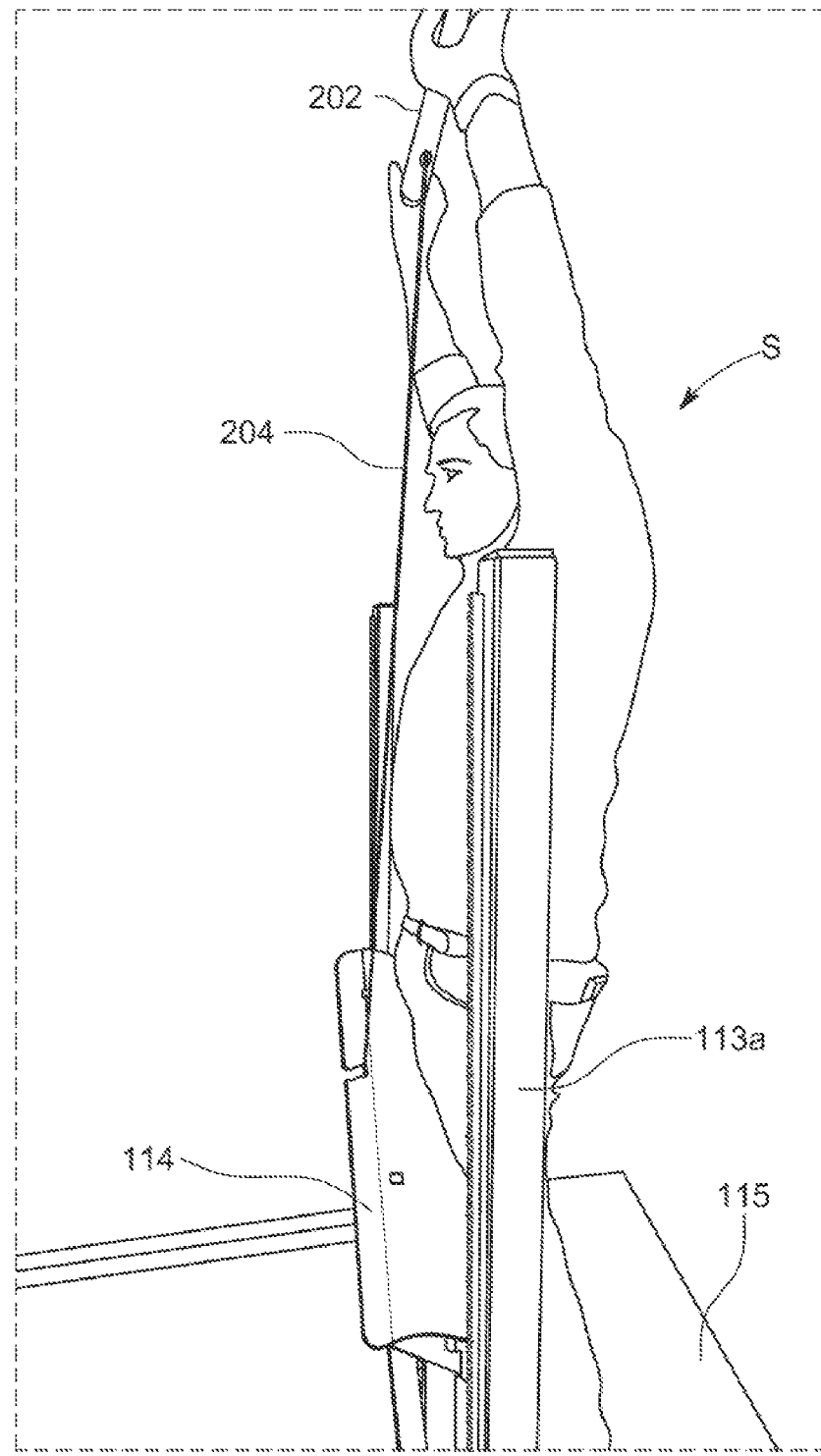
FIG. 14A is a side elevation view of a subject in the start position (Max Y) for performing the method for simulating, measuring and recording a subject's ability to perform a varying range of barrier reaches incorporating the apparatus shown in FIGS. 9-13.

A method for measuring a subject's ability to perform a varying range of barrier reaches is also provided according to the invention. As shown in FIG. 14A, the subject S is positioned at the barrier 114. The subject S is instructed to stand as far forward on the foot plate 115 of the variable barrier reach instrument 112 as possible, coming into contact with the barrier 114. The subject S grasps the bar 202 which is connected to the linear encoder 206 and rotary encoder 212 by cable 204. The subject S raises the bar 202 overhead as high as possible, without over-extending the shoulders or elbows.

Figure 14B:
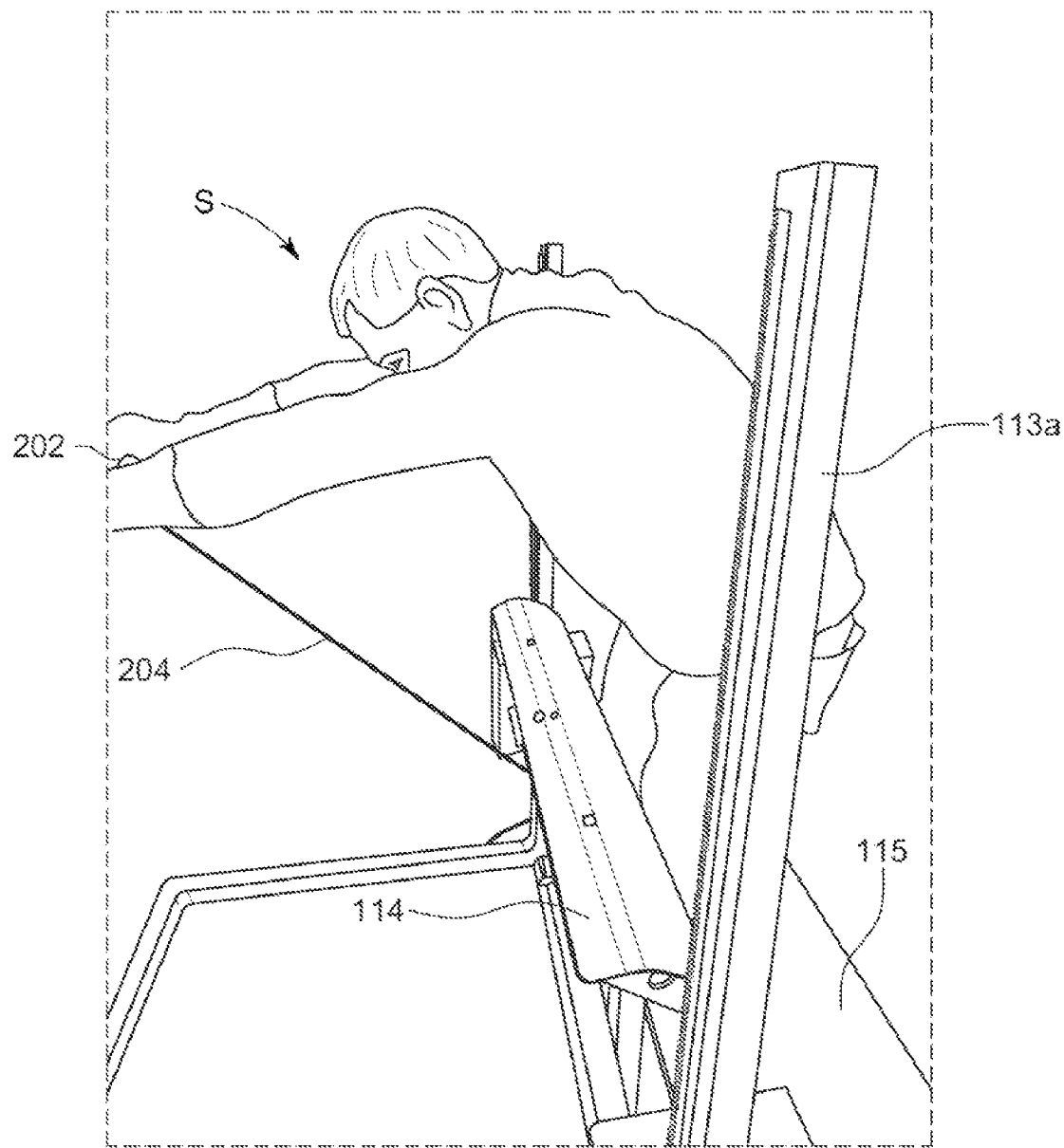
FIG. 14B is a side elevation view of a subject in an intermediate position for performing the method for simulating, measuring and recording a subject's ability to perform a varying range of barrier reaches incorporating the apparatus shown in FIGS. 9-13.
Figure 14C:
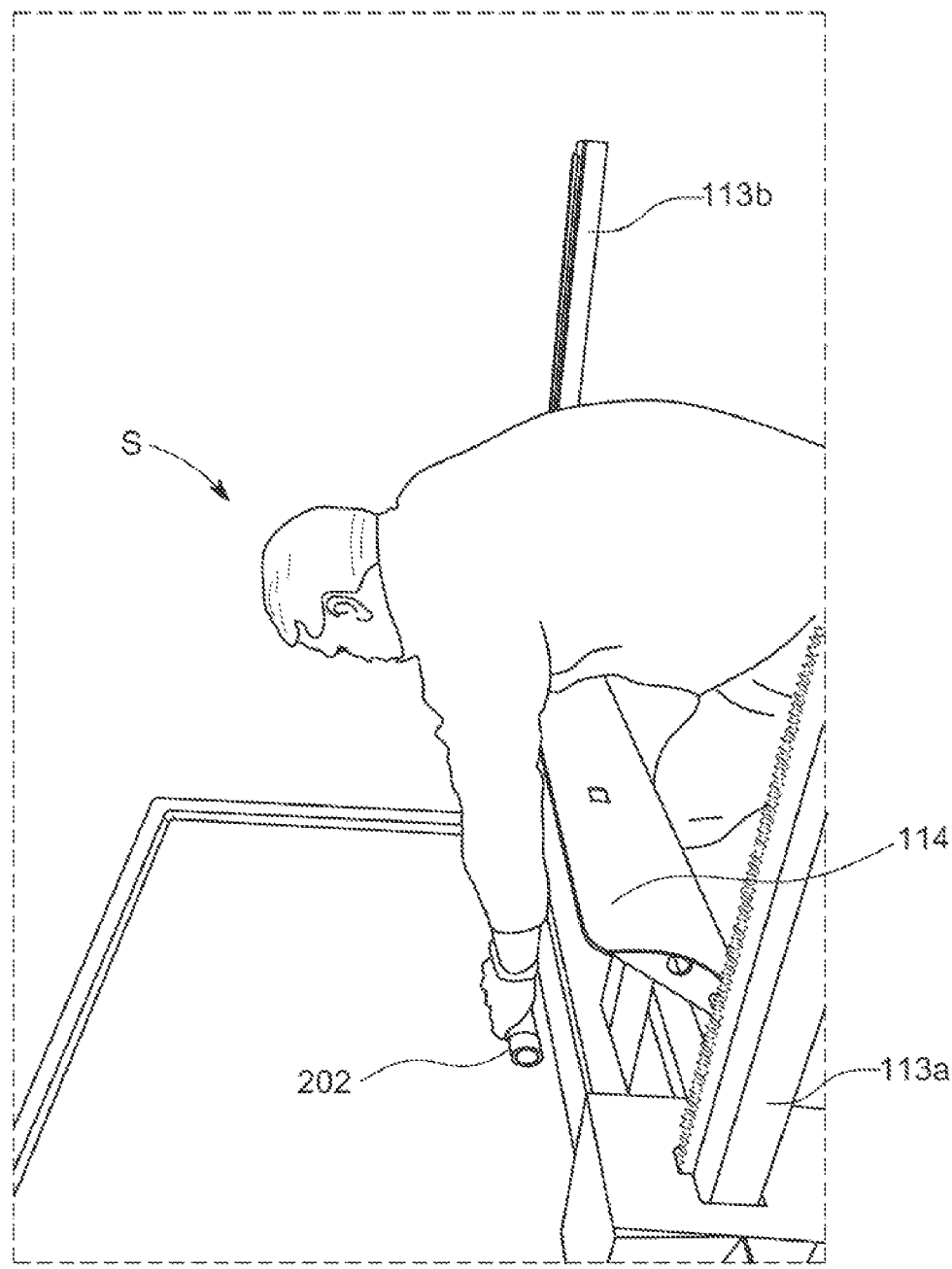
FIG. 14C is a side elevation view of a subject in the finish position (Min Y) for performing the method for simulating, measuring and recording a subject's ability to perform a varying range of barrier reaches incorporating the apparatus shown in FIGS. 9-13.

Next, as shown in FIG. 14B, the subject S bends forward, while maintaining contact with the barrier 114. The subject S continues to bend forward, reaching as far forward and downward as possible until the subject reaches the maximum point of extension, Min Y, as shown in FIG. 14C. Balance should be maintained throughout the entire arc, and the subject's heels should remain in contact with the foot plate 115. The subject S then returns to an upright position.

The resulting arc A includes a plurality of data points, Max Y, Point 1, Max X, Point 2 and Min Y, which are sensed and determined by the linear encoder 206 and rotary encoder 212 and then converted into an interpolated arc A' by the processor 214 reflecting the subject's reach at a measured barrier height which can be displayed on the user interface module. The user U may also select to start and stop the measurements from the user interface module 220 to start and stop the measuring of data at the appropriate times during this process.

The method further includes the step of adjusting the height of the barrier 214 and repeating the steps enumerated above for the new barrier height. This may be done at multiple barrier heights to obtain data for a subject S at several different barrier heights. According to one preferred embodiment of the method of the present invention, the process is repeated at seven pre-set variable heights ranging in 6-inch increments from 24 inches to 60 inches. Heights above and below that range are also anticipated depending on the specific needs of the test and the height of the subject.

While the sensing and recording device 200 is described herein as being a linear encoder and rotary encoder, it is anticipated, and is within the scope and intent of the invention to utilize other electronic marking and sensing devices, including, but not limited to the use of optical sensors and/or video capture devices, such that the data can be directly read and recorded to the software program. Similarly, while the barrier 114 and bar 202 are described herein as a "physical" barrier and a "physical" bar, it is also within the scope of the invention to provide a virtual barrier and/or a virtual bar for use in connection with the method of the invention. Also, while the invention is described in terms of a two arm reach measurement, it is within the scope of the invention to perform the same set of measurements for a single handed reach. Further, this detailed description, and particularly the specific details of the exemplary embodiment disclosed, is given primarily for clearness of understanding and no unnecessary limitations are to be understood therefrom, for modifications will become evident to those skilled in the art upon reading this disclosure and may be made without departing from the spirit or scope of the claimed invention.

We claim:

1. An apparatus for simulating, measuring and recording a subject's ability to perform a varying range of barrier reaches comprising:
   a variable barrier reach instrument for simulating an actual barrier that the subject may lean against in performing a work task, said variable barrier reach instrument including a physical barrier having a substantially horizontal upper surface at a height above a base point;
   a sensing and recording device positioned proximate to the variable barrier reach instrument for sensing and recording a plurality of barrier reach data points as the subject bends forward against the physical barrier;
   a computer and an associated software program into which said recorded data points are entered, an algorithm contained within said software program that generates an interpolated arc reflecting said subject's reach at said physical barrier height from said recorded data points, and storage means associated with said computer for storing said interpolated arc and recorded data points.

2. The apparatus of claim 1 wherein the height of said physical barrier is adjustable.

3. The apparatus of claim 2 wherein the variable barrier reach instrument includes a plurality of pre-set variable heights.

4. The apparatus of claim 3 wherein the variable barrier reach instrument includes seven pre-set variable heights ranging in 6-inch increments from 24 inches to 60 inches.

5. The apparatus of claim 2, further comprising a drive mechanism attached to said physical barrier for moving the physical barrier vertically relative to the base point.

6. The apparatus of claim 5, further comprising a pair of vertical posts, spaced a distance apart, said physical barrier positioned between said vertical posts.

7. The apparatus of claim 6, further comprising a pair of gear boxes associated with said pair of vertical posts, respectively, said gear boxes being affixed to said physical barrier and configured for vertical translational movement relative to said vertical posts.

8. The apparatus of claim 7, further comprising a motor attached to one of said gear boxes for imparting motion to said pair of gearboxes and the physical barrier relative to the vertical posts.

9. The apparatus of claim 1 wherein the sensing and recording device comprises:
    a bar for grasping by the subject; and
    one or more encoders attached to said bar for sensing and recording linear and angular displacement of the bar.

10. The apparatus of claim 9, further comprising a cable having a first end attached to said bar and a second end attached to said one or more encoders.

11. The apparatus of claim 10, wherein said one or more encoders comprises:
    a linear encoder attached to a second end of said cable, said linear encoder configured to sense and record an amount of cable that is withdrawn from the linear encoder at various times; and
    a rotary encoder slidably engaging the cable along a length thereof, said rotary encoder configured to sense and record the angular displacement of the bar and cable at various times.

12. The apparatus of claim 1 wherein the plurality of data points include at least:
    a start point (Max Y) where the subject is positioned with its feet at the base point and its hands grasping the bar extended overhead as high as possible;
    an end point (Min Y) where the subject is positioned bent forward against the physical barrier at the lowest point in the vertical (y) axis above the base point;
    a furthest horizontal point (Max X) at a point on the arc in the horizontal (x) axis farthest from the base point;
    a first point that is midway between the start point and the furthest horizontal point; and
    a second point that is midway between the end point and the furthest horizontal point.

13. A method for simulating, measuring and recording a subject's ability to perform a varying range of barrier reaches comprising the steps of:
    (1) positioning the subject at a variable barrier reach instrument for simulating an actual barrier that the subject may lean against in performing a work task, said variable barrier reach instrument having a physical barrier having a substantially horizontal upper surface at a height above a base point;
    (2) having the subject grasp a bar that is operatively connected to a sensing and recording device positioned proximate to the physical barrier;
    (3) having the subject raise the bar overhead such that the sensing and recording device is operatively engaged;
    (4) having the subject bend forward, while continuing to grasp the bar with outstretched arms, extending the bar in an arc until the subject has reached a lowest point nearest to the base point;
    (5) using said sensing and recording device to sense and record in a software program associated with a computer a plurality of data points along an arc that is generated as the subject bends forward;
    (6) applying an algorithm contained in the software program to said recorded data points to generate an interpolated arc reflecting said subject's reach at said physical barrier height from said recorded data points, and
    (7) storing said interpolated arc and recorded data points in storage means associated with said computer.

14. The method of claim 13 further comprising the further step of adjusting the height of the physical barrier and repeating steps (1)-(6) at the adjusted physical barrier height.

15. The method of claim 14 wherein steps (1)-(6) are repeated sequentially for seven pre-set variable heights ranging in 6-inch increments from 24 inches to 60 inches.

16. The method of claim 14 wherein the height of the physical barrier is adjusted by actuating a drive mechanism attached to said physical barrier to move the physical barrier vertically relative to the base point.

17. The method of claim 13 wherein the step of identifying and recording said plurality of data points comprises the steps of:
    identifying and recording a start point (Max Y) on the sensing and recording device where the subject is positioned with its feet at the base point and its hands grasping the bar extended overhead as high as possible;
    identifying and recording an end point (Min Y) on the sensing and recording device where an arc sensed and recorded on the two-dimensional grid as the subject bends forward against the physical barrier comes to an end at the lowest point in the vertical (y) axis above the base point;
    identifying and recording a furthest horizontal point (Max X) at a point on the arc in the horizontal (x) axis farthest from the base point;
    identifying and recording a first point that is midway between the start point and the furthest horizontal point; and
    identifying and recording a second point that is midway between the end point and the furthest horizontal point.

18. The method of claim 13 wherein the step of positioning a subject at a variable barrier reach instrument includes having the subject come into contact with said physical barrier.

19. The method of claim 13 wherein the step of using said sensing and recording device to sense and record comprises using one or more encoders attached to said bar for sensing and recording linear and angular displacement of the bar.

20. The method of claim 19 wherein the step of using one or more encoders comprises using a linear encoder attached to the bar by a cable to sense and record an amount of cable that is withdrawn from the linear encoder at various times; and using a rotary encoder slidably engaging the cable along a length thereof to sense and record the angular displacement of the bar and cable at various times.

* * * * *